United States Patent [19]

Merrill, deceased et al.

[11] Plant 4,970

[45] Jan. 4, 1983

[54] PEACH TREE (A3-10)

[76] Inventors: Grant Merrill, deceased, late of Red Bluff, Calif.; by Lucile B. Merrill, executrix, 325 Breese Ave., Red Bluff, Calif. 96080

[21] Appl. No.: 284,541

[22] Filed: Jul. 20, 1981

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is large, vigorous, and spreading; foliated with large, lanceolate leaves having a finely serrate margin, a petiole of medium length and thickness, and medium size, reniform glands; blooms from medium size, conic, plump, pubescent buds; the flowers, medium in blooming period compared with other varieties, being of medium size, and pink; and is a regular and very productive bearer of medium but variable size, round truncate, clingstone fruit having yellow skin substantially overspread with red, yellow flesh mottled with red adjacent the skin, and an amber stone.

1 Drawing Figure

BACKGROUND OF THE VARIETY

1. Field of the Invention

In an extensive plant breeding program, Grant Merrill, originator and now deceased, originated a large number of new and distinct varieties of fruit trees, and which included the herein-claimed variety of peach tree. Such plant breeding program was undertaken in originator's experimental orchard located near Exeter, Tulare County, Calif.

2. Prior Varieties

Among the existent varieties of peach trees which were known to originator, particular reference is made to Gemfree (U.S. Plant Pat. No. 1,409) and June Lady (U.S. Plant Pat. No. 3,022) hereinafter mentioned for the purpose of comparison.

ORIGIN OF THE VARIETY

The present variety of peach tree was originated, in the aforesaid experimental orchard, as an open-pollinated seedling of the June Lady.

ASEXUAL REPRODUCTION OF THE VARIETY

When such open-pollinated seedling matured as a bearing tree, and its novelty and commercial potential were recognized by originator, the variety was asexually reproduced by originator by grafting on suitable rootstock in the aforesaid experimental orchard. The asexual reproduction of the variety ran true, in all respects, to the original tree of the variety.

SUMMARY OF THE VARIETY

The herein-claimed new and distinct variety of peach tree is, characteristically, large, vigorous, and spreading; foliated with large, lanceolate leaves having a finely serrate margin, a petiole of medium length and thickness, and medium size, reniform glands; blooms from medium size, conic, plump, pubescent buds; the flowers, medium in blooming period compared with other varieties, being of medium size, and pink; and is a regular and very productive bearer of medium but variable size, round truncate, clingstone fruit having yellow skin substantially overspread with red, yellow flesh mottled with red adjacent the skin, and an amber stone.

The herein-claimed new and distinct variety of peach tree, while similar in tree characteristics including growth pattern, is particularly distinguishable — in comparison with the Gemfree — by fruit which is more round in shape and has a darker red blush color of the skin; the fruit ripening approximately with or slightly later than the fruit of the Gemfree.

BRIEF DESCRIPTION OF THE DRAWING

The drawing is an illustration, by photographic reproduction in color, of separate fruit of the variety; one of the fruit being half-cut away to expose the flesh and stone.

DESCRIPTION OF THE VARIETY

The botanical details of this new and distinct variety of peach tree — with color definitions (except those in common color terms) referenced to Maerz and Paul Dictionary of Color (second edition) — are as follows:

Tree:
- *Size.*—Large.
- *Vigor.*—Vigorous.
- *Form.*—Spreading.
- *Production.*—Productive. Sets heavy crop requiring thinning for commercial sizing.
- *Bearing.*—Regular bearer.

Trunk:
- *Size.*—Stocky.
- *Texture.*—Medium.

Branches:
- *Size.*—Medium.
- *Texture.*—Medium.
- *Color.*—Brown (8-H-11).

Lenticels:
- *Number.*—Numerous.
- *Size.*—1–2×4–6 mm.

Leaves:
- *Size.*—Large. Length range — 190–200 mm. Width range — 48–52 mm.
- *Form.*—Lanceolate.
- *Color.*—Top side — Medium green (24-L-8). Under side — Lighter green (23-L-7).
- *Margin.*—Finely serrate.
- *Petiole.*—Medium length (15 mm.). Medium thickness (2 mm.).

*Glands.*—Leaf glands: Average number — 2. Opposite. Reniform. Petiole glands: Number — 2–3. Alternate. Medium size (0.5×1 mm.). Reniform. Green (22-J-4).

Flower buds:

*Size.*—Medium.

*Form.*—Conic. Plump.

*Pubescence.*—Pubescent.

Flowers:

*Blooming period.*—Date of first bloom: Mar. 4th. Date of approximate full bloom: Mar. 11th. Petal fall: Mar. 17th. Medium, as compared with other varieties.

*Size.*—Medium (20 mm. in diameter).

*Color.*—Top side — Pink (50-H-1). Under side — Pink (50-H-1).

*Pistils.*—Number — 1.

*Stamens.*—Number — 34–35.

Fruit:

*Maturity when described.*—Eating ripe.

*Date of first picking.*—June 13, 1979.

*Date of last picking.*—June 20, 1979.

*Harvest date for fresh shipping.*—June 15th–16th.

*Size.*—Variable. Medium. Axial diameter range — 55–56 mm. Range transversely in suture plane — 66–67 mm.

*Form.*—Variable. Round truncate with equal sides.

*Suture.*—Distinct. Shallow. Extends from base over entire circumference with slight depression beyond pistil point.

*Ventral surface.*—Rounded slightly.

*Cavity.*—Flaring. Average depth — 12 mm. Average breadth — 20 mm.

*Base.*—Truncate.

*Apex.*—Rounded.

*Pistil point.*—Oblique.

*Stem.*—Average length — 12 mm. Average caliper — 4 mm.

Skin:

*Thickness.*—Medium.

*Texture.*—Medium.

*Tendency to crack.*—None.

*Down.*—Moderate.

*Color.*—Ground color: Yellow (10-J-6). Blush: Red (7-L-8).

Flesh:

*Color.*—Yellow (10-J-6) mottled with red (5-L-9) adjacent the skin and to one-half the depth of the flesh. Surface of pit cavity: Cream (9-E-1).

*Juice.*—Abundant.

*Texture.*—Medium.

*Fibers.*—Few. Fine.

*Ripens.*—Evenly.

*Flavor.*—Sub-acid. Delicate.

*Aroma.*—Distinct.

*Eating quality.*—Good.

Stone:

*Type.*—Clingstone. Adheres to flesh over entire surface.

*Size.*—Medium. Average length — 32 mm. Average breadth — 24 mm. Average thickness — 19 mm.

*Form.*—Oval.

*Base.*—Straight.

*Hilum.*—Narrow.

*Apex.*—Acute.

*Sides.*—Unequal.

*Surface.*—Irregularly furrowed near base. Ridged near base. Pitted toward base.

*Ridges.*—Jagged toward apex.

*Pits.*—Elongated.

*Ventral edge.*—Thin, with wing in middle.

*Dorsal edge.*—Narrow, with shallow groove toward base.

*Color.*—Amber (12-F-9).

*Tendency to split.*—Slight.

Use: Market; dessert.

Keeping quality: Good.

Shipping quality: Good.

The peach tree and its fruit herein described may vary in slight detail due to climatic and soil conditions under which the variety may be grown; the present description being of the variety as grown in the Central Valley of California.

It is claimed:

1. A new and distinct variety of peach tree, substantially as illustrated and described, which has general similarity in tree to the Gemfree but bears clingstone fruit which, in particular comparison with the fruit of the Gemfree, is more round in shape and has a darker red blush color of the skin; the fruit ripening approximately with or slightly later than the fruit of the Gemfree.

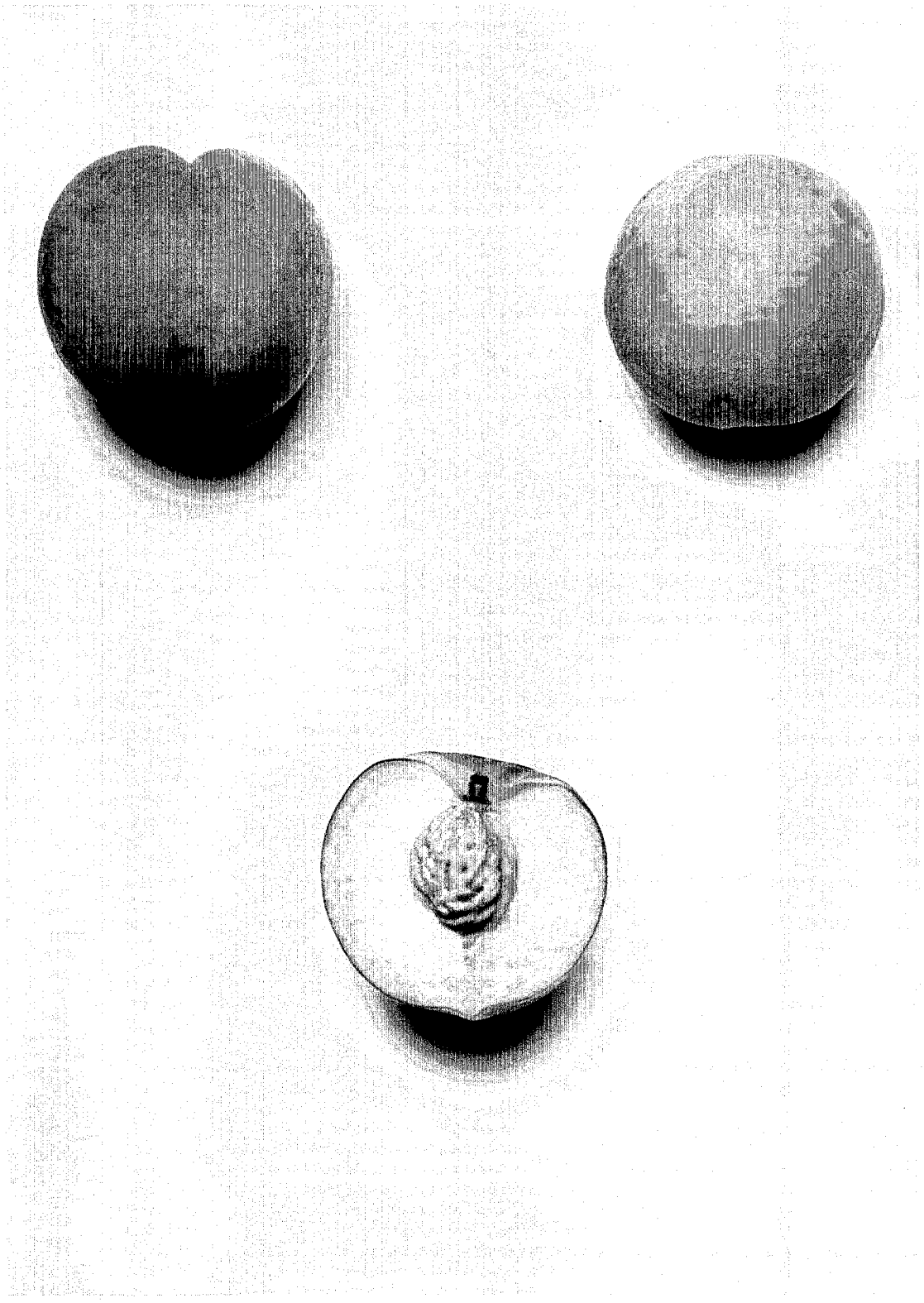

* * * * *